(12) United States Patent
Al-Huwaider et al.

(10) Patent No.: US 11,460,443 B2
(45) Date of Patent: Oct. 4, 2022

(54) FLUID ANALYSIS SYSTEMS AND METHODS IN OIL AND GAS APPLICATIONS

(71) Applicant: Saudi Arabian Oil Company, Dhahran (SA)

(72) Inventors: Mustafa A. Al-Huwaider, Dhahran (SA); Shouxiang Mark Ma, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 19 days.

(21) Appl. No.: 17/178,959

(22) Filed: Feb. 18, 2021

(65) Prior Publication Data
US 2022/0260530 A1    Aug. 18, 2022

(51) Int. Cl.
*G01N 29/024* (2006.01)
*G01C 19/00* (2013.01)
*E21B 49/08* (2006.01)

(52) U.S. Cl.
CPC ....... *G01N 29/024* (2013.01); *E21B 49/0875* (2020.05); *G01C 19/00* (2013.01); *G01N 2291/011* (2013.01); *G01N 2291/0222* (2013.01); *G01N 2291/0224* (2013.01); *G01N 2291/105* (2013.01)

(58) Field of Classification Search
CPC .. E21B 49/0875; G01C 19/00; G01N 29/024; G01N 29/02; G01N 2291/011; G01N 2291/022; G01N 2291/025; G01N 2291/0222; G01N 2291/0224; G01N 2291/105
See application file for complete search history.

(56) References Cited

U.S. PATENT DOCUMENTS

| | | | |
|---|---|---|---|
| 5,531,112 A | * | 7/1996 | Young ................ G01N 33/2823 166/117.7 |
| 5,719,329 A | | 2/1998 | Jepson et al. |
| 6,028,307 A | | 2/2000 | Young et al. |
| 6,550,345 B1 | | 4/2003 | Letton |

(Continued)

OTHER PUBLICATIONS

"Multiple Array Production Suite (MAPS)," Proactive Diagnostic Services, Well Integrity Diagnostic Specialists, Brochure, 2 pages.
(Continued)

*Primary Examiner* — Suman K Nath
(74) *Attorney, Agent, or Firm* — Fish & Richardson P.C.

(57) ABSTRACT

A fluid analysis system for characterizing a multiphase fluid includes a first set of acoustic probes disposed at a first angular position about a central axis of the fluid analysis system and oriented to direct first sound waves along a first direction that is parallel to the central axis, a second set of acoustic probes disposed at a second angular position about the central axis that is opposite to the first angular position and oriented to direct second sound waves along the first direction, a third set of acoustic probes spanning the central axis and oriented to direct third sound waves along a second direction that is perpendicular to the central axis, and an analysis unit. The analysis unit is configured to determine a location of a fluid interface within the multiphase fluid based on first, second, and third parameters respectively associated with the first, second, and third sounds waves.

24 Claims, 6 Drawing Sheets

(56) References Cited

U.S. PATENT DOCUMENTS

| | | | |
|---|---|---|---|
| 8,978,481 B2 | 3/2015 | Powell et al. | |
| 9,383,476 B2 | 7/2016 | Trehan et al. | |
| 2004/0194539 A1* | 10/2004 | Gysling | G01N 29/348 |
| | | | 73/61.45 |
| 2005/0125169 A1* | 6/2005 | Loose | G01F 1/3259 |
| | | | 702/45 |
| 2007/0157737 A1* | 7/2007 | Gysling | G01F 15/005 |
| | | | 73/861.23 |
| 2008/0173100 A1 | 7/2008 | Davis | |
| 2019/0196041 A1* | 6/2019 | Yao | G01V 1/50 |
| 2019/0277806 A1 | 9/2019 | Huang | |
| 2020/0208514 A1* | 7/2020 | Swett | G01F 1/69 |

OTHER PUBLICATIONS

Bauldauff et al., "Profiling and quantifying complex multiphase flow," Oilfield Review, Autumn 2004, 10 pages.

Liu, "Acoustic Properties of Reservoir Fluids," A Dissertation Submitted to the Department of Geophysics and Committee on Graduate Studies of Stanford University in Partial Fulfillment of the Requirements for the Degree of Doctor of Philosophy, Jun. 1998, 111 pages.

McCoy et al., "Analyzing Well Performance VI," Southwestern Petroleum Short Course Association, Lubbock, 1973, 9 pages.

Oilproduction.net [online], "Acoustic Velocity for Natural Gas," retrieved on Jan. 7, 2021, retrieved from URL <http://oilproduction.net/files/Acoustic%20Velocity%20for%20Natural%20Gas.pdf>, 6 pages.

Thomas et al., "Determination of Acoustic Velocities for Natural Gas," SPE 2579, Society of Petroleum Engineers (SPE), Journal of Petroleum Technology 22;07, Jul. 1970, 7 pages.

Wang et al., "Acoustic Velocities in Petroleum Oils," SPE 18163 MS/ SPE 18163 PA, Society of Petroleum Engineers (SPE), presented at the SPE Annual Technical Conference and Exhibition, Oct. 2-5, 1988, 15 pages.

PCT International Search Report and Written Opinion in International Appln. No. PCT/US2022/016968, dated May 18, 2022, 15 pages.

Oddie, "Flow-Rate Measurement in Two-Phase Flow," Annual Review of Fluid Mechanics, Jan. 2004, 36(1): 149-172, 26 pages.

* cited by examiner

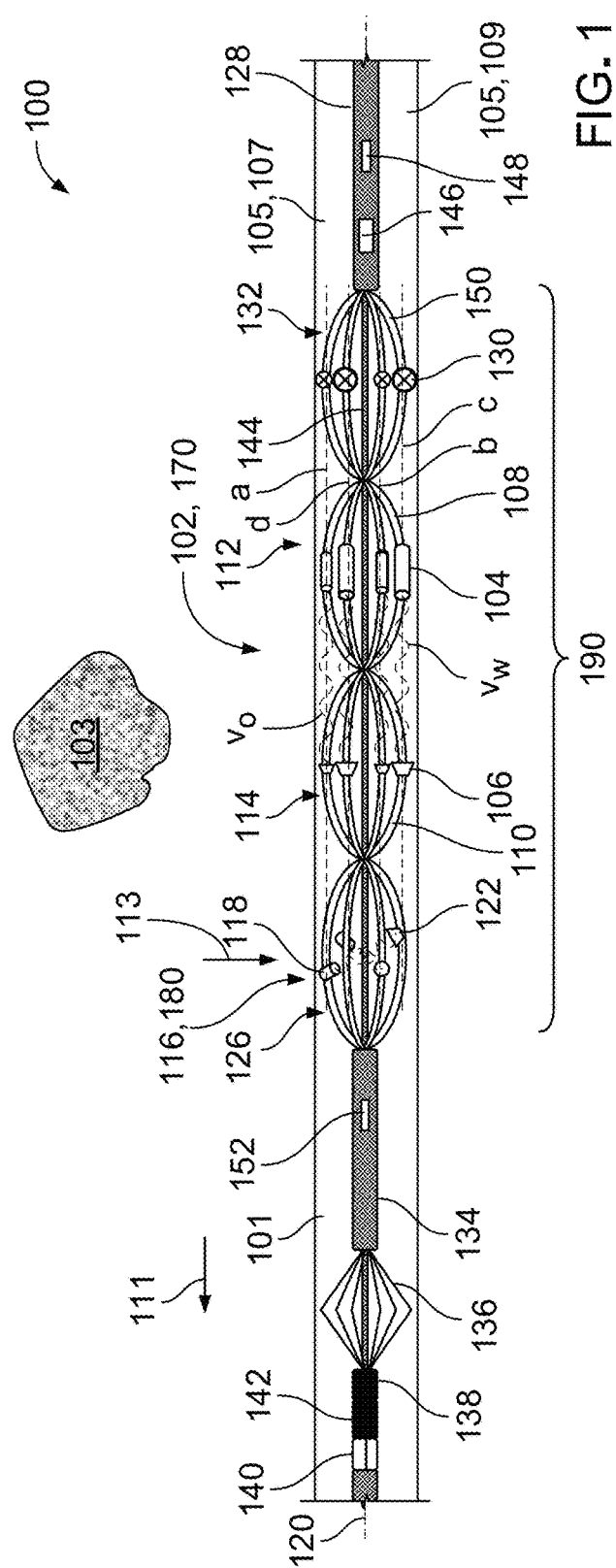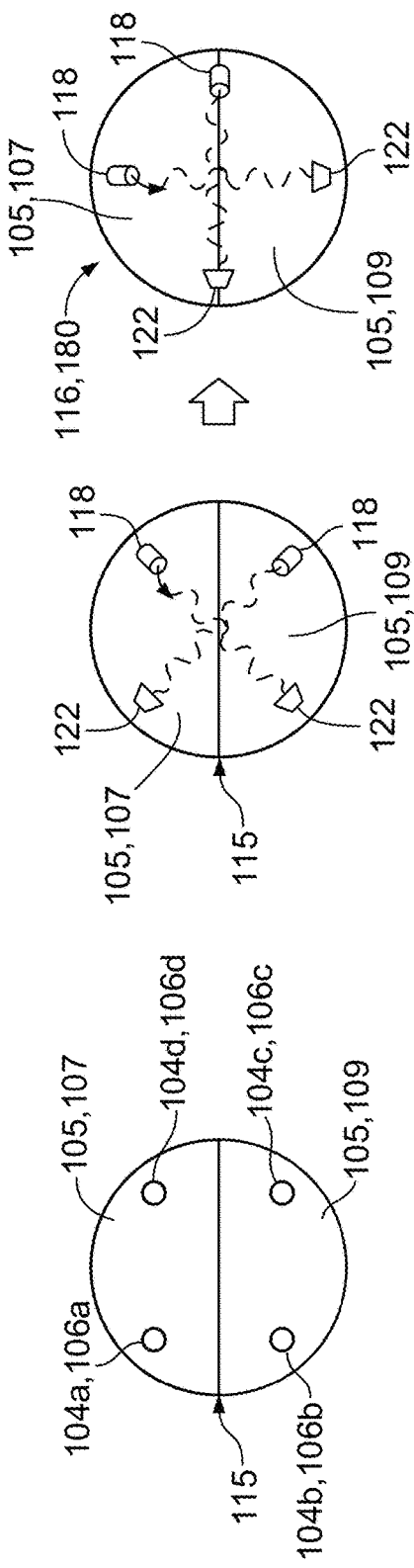

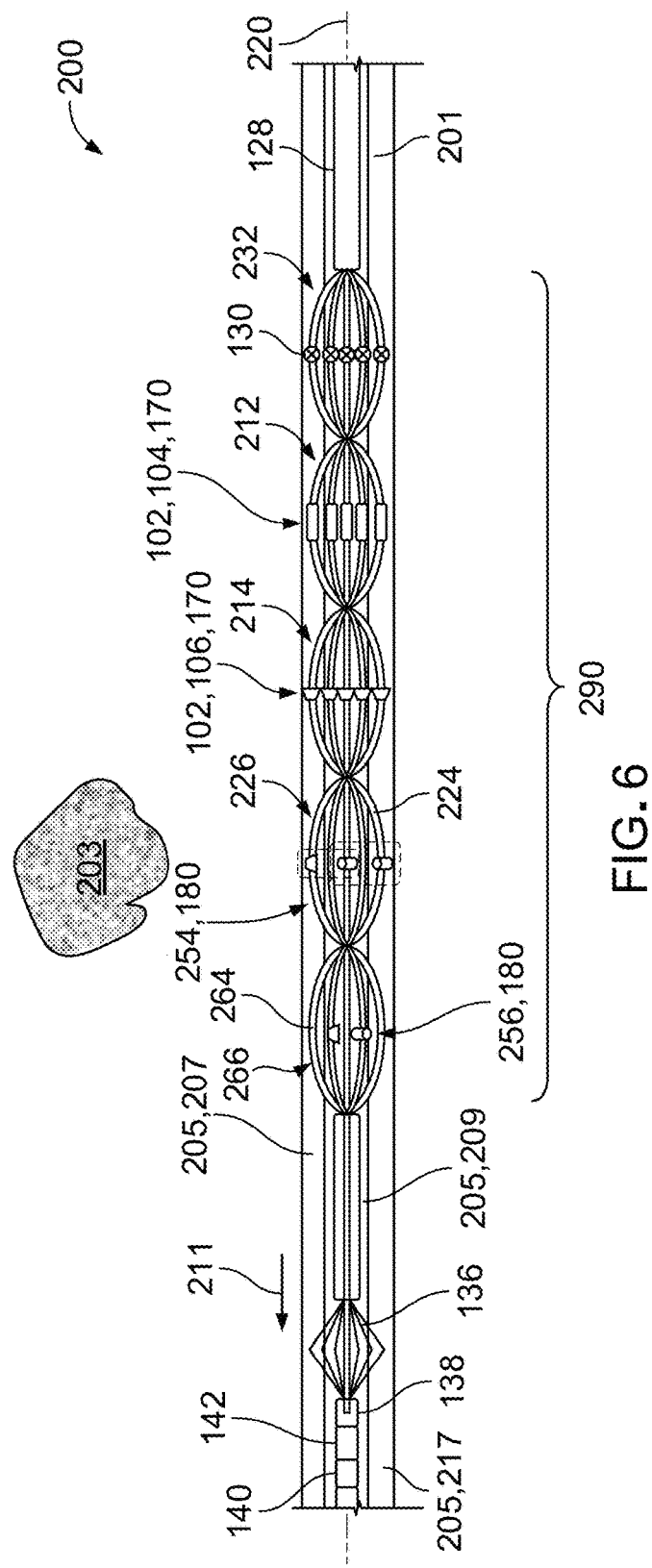
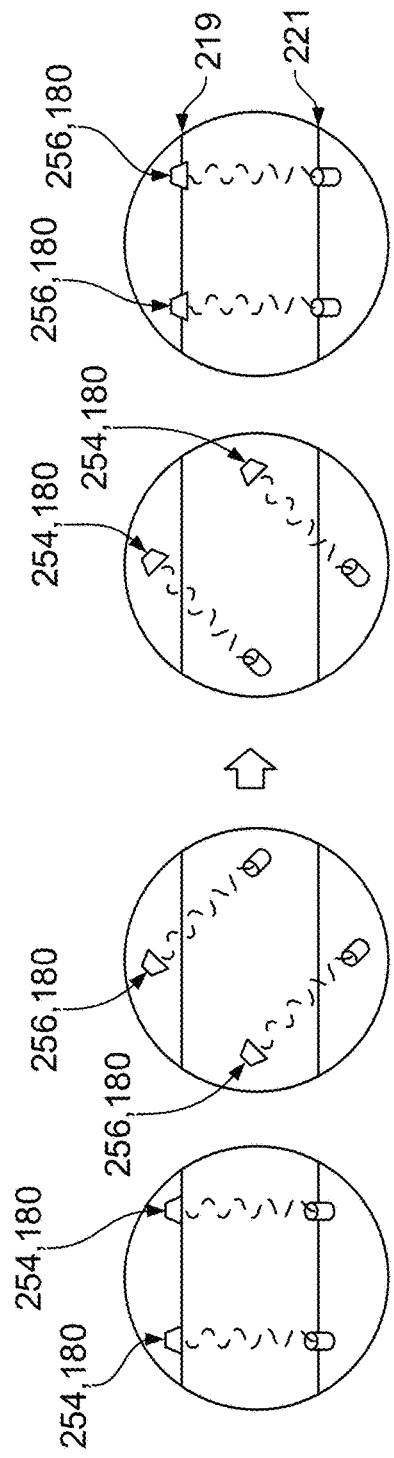
FIG. 6
FIG. 7

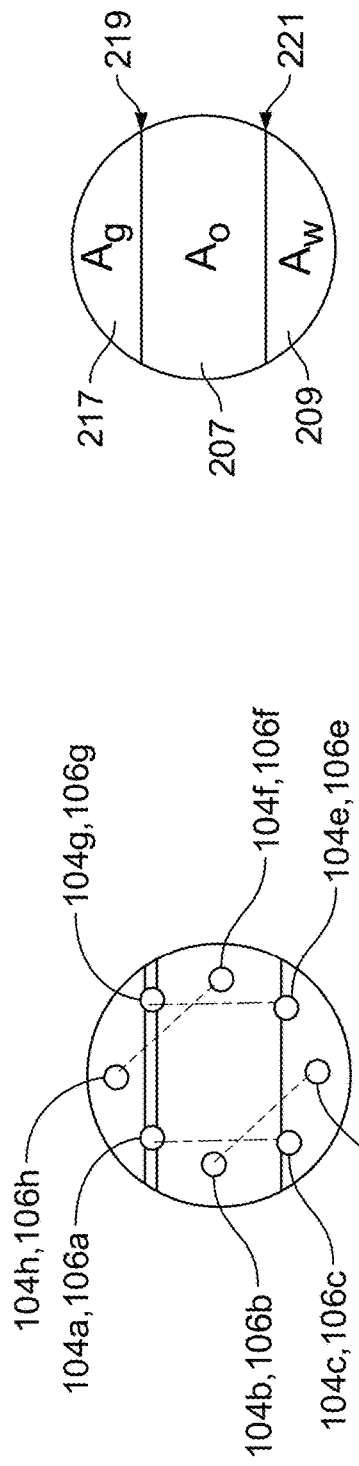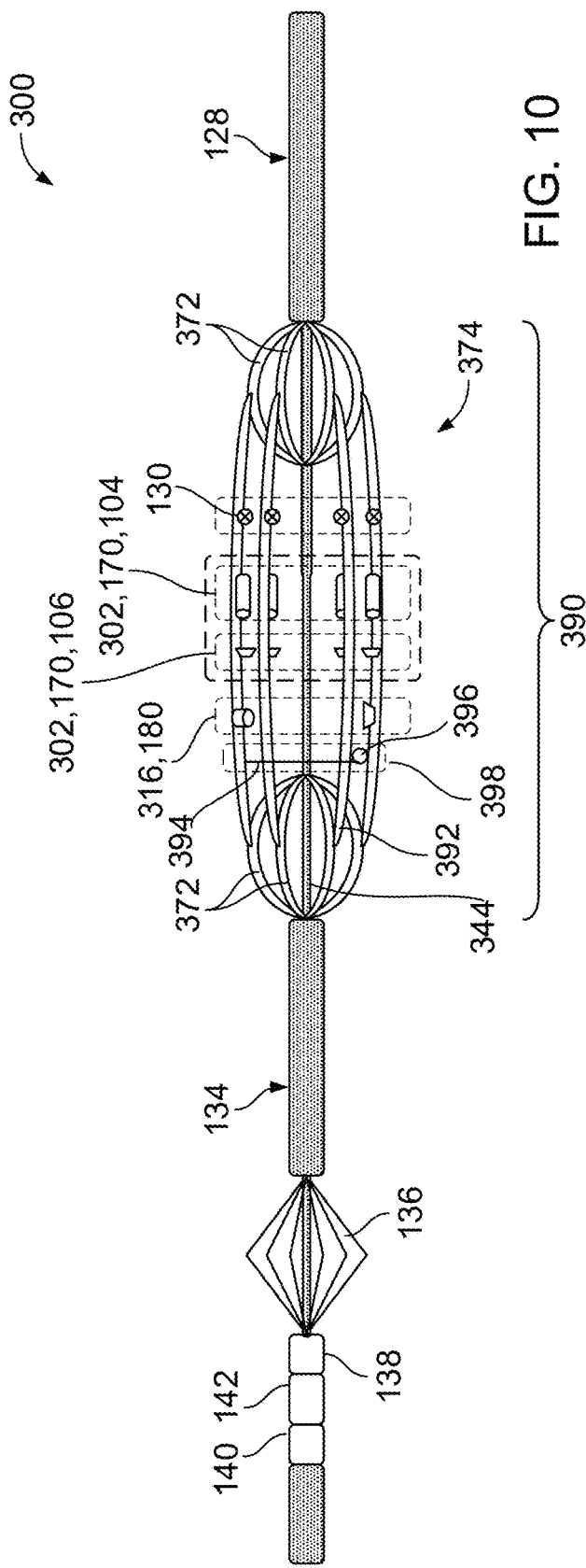

FLUID ANALYSIS SYSTEMS AND METHODS IN OIL AND GAS APPLICATIONS

TECHNICAL FIELD

This disclosure relates to fluid analysis systems and related methods of determining fluid holdups within a multiphase fluid flowing in horizontal wells or surface pipes based on accurate determinations of fluid interface locations within the multiphase fluid.

BACKGROUND

When a multiphase fluid flows in a horizontal well, the fluid segregates due to gravity. For example, gas may flow along a top region of the well in a first phase, water may flow along a bottom region of the well in a second phase, and oil may flow between the gas and water along a middle region of the well in a third phase. In order to accurately calculate fluid holdups (for example, fluid fractions of the gas, oil, and water) within the well, vertical positions of fluid interfaces between adjacent phases should be accurately determined. However, accurate determination of the positions of the fluid interfaces falls short of ideal assessment due to design limitations of conventional sensing and detection systems.

SUMMARY

This disclosure relates to fluid analysis systems that are designed to determine fluid fractions (for example, fluid holdups) of a multiphase fluid flowing in a horizontal wellbore based on an accurate determination of fluid interfaces within the multiphase fluid. An example fluid analysis system includes multiple sets of parallel acoustic probes that are oriented parallel to fluid interfaces within the multiphase fluid and multiple sets of perpendicular acoustic probes that are oriented perpendicular to the fluid interfaces. Each set of parallel acoustic probes and each set of perpendicular acoustic probes includes a transmitter that transmits a sound wave and a corresponding receiver that receives the sound wave. An angular spacing between the sets of parallel acoustic probes ensures that, irrespective of a rotational position of the fluid analysis system within the wellbore, at least one set of the parallel acoustic probes is always located substantially entirely within each fluid of the multiphase fluid to determine an acoustic wave speed within each fluid. Additionally, orientations of the sets of perpendicular acoustic probes with respect to each other ensure that, irrespective of the rotational position of the fluid analysis system within the wellbore, each fluid interface within the multiphase fluid is spanned by at least one set of perpendicular acoustic probes to determine fluid interface locations based on the previously determined acoustic wave speeds within each fluid. Accurate determination of the fluid interface locations can be used by the fluid analysis system to accurately determine the fluid fractions of the multiphase fluid.

In one aspect, a fluid analysis system for characterizing a multiphase fluid includes a first set of acoustic probes disposed at a first angular position about a central axis of the fluid analysis system and oriented to direct first sound waves along a first direction that is parallel to the central axis, a second set of acoustic probes disposed at a second angular position about the central axis that is opposite to the first angular position and oriented to direct second sound waves along the first direction, a third set of acoustic probes spanning the central axis and oriented to direct third sound waves along a second direction that is perpendicular to the central axis, and an analysis unit. The analysis unit is configured to determine a first parameter associated the first sound waves, a second parameter associated with the second sound waves, and a third parameter associated with the third sound waves, and to determine a location of a fluid interface within the multiphase fluid based on the first, second, and third parameters.

Embodiments may provide one or more of the following features.

In some embodiments, the analysis unit is further configured to determine a first fluid fraction of a first fluid of the multiphase fluid and a second fluid fraction of a second fluid of the multiphase fluid based on the location of the fluid interface.

In some embodiments, the first and second sets of acoustic probes are located at a first axial position along the central axis.

In some embodiments, the third set of acoustic probes is located at a second axial position along the central axis that is spaced apart from the first axial position.

In some embodiments, the first set of acoustic probes includes a first transducer and a first receiver that are tuned to a first unique frequency, wherein the second set of acoustic probes includes a second transducer and a second receiver that are tuned to a second unique frequency, and wherein the third set of acoustic probes includes a third transducer and a third receiver that are tuned to a third unique frequency.

In some embodiments, the first parameter includes a first velocity at which the first sound waves travel between the first transducer and the first receiver, and the second parameter includes a second velocity at which the second sound waves travel between the second transducer and the second receiver.

In some embodiments, the third parameter includes a time period taken for the third sound waves to travel between the third transducer and the third receiver.

In some embodiments, the analysis unit is further configured to determine a first distance traveled by the third waves between the third transducer and the fluid interface and a second distance traveled by the third waves between the fluid interface and the third receiver to define the location of the fluid interface.

In some embodiments, the analysis unit is further configured to determine a first fluid fraction of a first fluid of the multiphase fluid and a second fluid fraction of a second fluid of the multiphase fluid based on the first and second distances traveled by the third waves.

In some embodiments, the fluid analysis system further includes a fourth set of acoustic probes spanning the central axis.

In some embodiments, the third and fourth sets of acoustic probes are located at the same axial position along the central axis, and the fourth set of acoustic probes is oriented to direct fourth sound waves along a third direction that is perpendicular to the central axis of the fluid analysis system and perpendicular to the second direction.

In some embodiments, the third and fourth sets of acoustic probes are both located at a first axial position along the central axis, and wherein the fourth set of acoustic probes is oriented to direct fourth sound waves along the second direction.

In some embodiments, the fluid analysis system further includes a fifth set of acoustic probes and a sixth set of acoustic probes that are both located at a second axial position along the central axis that is different from the first axial position and that are oriented to respectively direct fifth and sixth sound waves along a third direction that is perpendicular to the central axis of the fluid analysis system and that is angularly offset from the second direction.

In some embodiments, the fluid interface is a first fluid interface at a first location, and the analysis unit is further configured to determine a second location of a second fluid interface within the multiphase fluid.

In some embodiments, the fluid analysis system further includes a wave generator that transmits the first, second, and third sound waves respectively to the first, second, and third sets of acoustic probes.

In some embodiments, the fluid analysis system further includes a gyroscope that determines a rotational position of the fluid analysis system within a borehole.

In another aspect, a method of characterizing a multiphase fluid within a borehole includes transmitting, at a first set of acoustic probes disposed within a first fluid of the multiphase fluid, first sound waves along a first direction that is parallel to a fluid interface located between the first fluid and a second fluid of the multiphase fluid; transmitting, at a second set of acoustic probes disposed within the second fluid, second sound waves along the first direction; transmitting, at a third set of acoustic probes that spans the fluid interface, third sound waves along a second direction that is perpendicular to the fluid interface; determining, at an analysis unit, a first parameter associated the first sound waves, a second parameter associated with the second sound waves, and a third parameter associated with the third sound waves; and determining, at the analysis unit, a location of the fluid interface based on the first, second, and third parameters.

Embodiments may provide one or more of the following features.

In some embodiments, the method further includes determining, at the analysis unit, a first fluid fraction of the first fluid and a second fluid fraction of the second fluid based on the location of the fluid interface.

In some embodiments, the first parameter includes a first velocity at which the first sound waves travel within the first fluid, and the second parameter includes a second velocity at which the second sound waves travel within the second fluid.

In some embodiments, the third set of acoustic probes includes a transducer and a receiver, and the third parameter includes a time period taken for the third sound waves to travel between the transducer and the receiver.

In some embodiments, the method further includes determining, at the analysis unit, a first distance traveled by the third waves between the transducer and the fluid interface and a second distance traveled by the third waves between the fluid interface and the receiver to define the location of the fluid interface.

In some embodiments, the method further includes determining, at the analysis unit, a first fluid fraction of the first fluid and a second fluid fraction of the second fluid based on the first and second distances traveled by the third waves.

In some embodiments, the method further includes transmitting the first, second, and third sound waves from a wave generator respectively to the first, second, and third sets of acoustic probes.

In some embodiments, the method includes determining, at a gyroscope, a rotational position of the fluid analysis system within the borehole.

The details of one or more embodiments are set forth in the accompanying drawings and description. Other features, aspects, and advantages of the embodiments will become apparent from the description, drawings, and claims.

DESCRIPTION OF DRAWINGS

FIG. 1 is a side view of a fluid analysis system disposed within a two-phase fluid in a wellbore.

FIG. 2 is front cross-sectional view of an arrangement of parallel acoustic probes of the fluid analysis system of FIG. 1.

FIG. 3 is front cross-sectional view of an arrangement of perpendicular acoustic probes of the fluid analysis system of FIG. 1.

FIG. 6 is a side view of a fluid analysis system disposed within a three-phase fluid in a wellbore.

FIG. 7 is front cross-sectional view of an arrangement of perpendicular acoustic probes of the fluid analysis system of FIG. 6.

FIG. 8 is front cross-sectional view of an arrangement of parallel acoustic probes of the fluid analysis system of FIG. 6.

FIG. 9 illustrates an example case for which the fluid analysis system of FIG. 6 is used to characterize a three-phase fluid in a wellbore.

FIG. 10 is a side view of a fluid analysis system with a relatively compact design.

DETAILED DESCRIPTION

Figure 4:
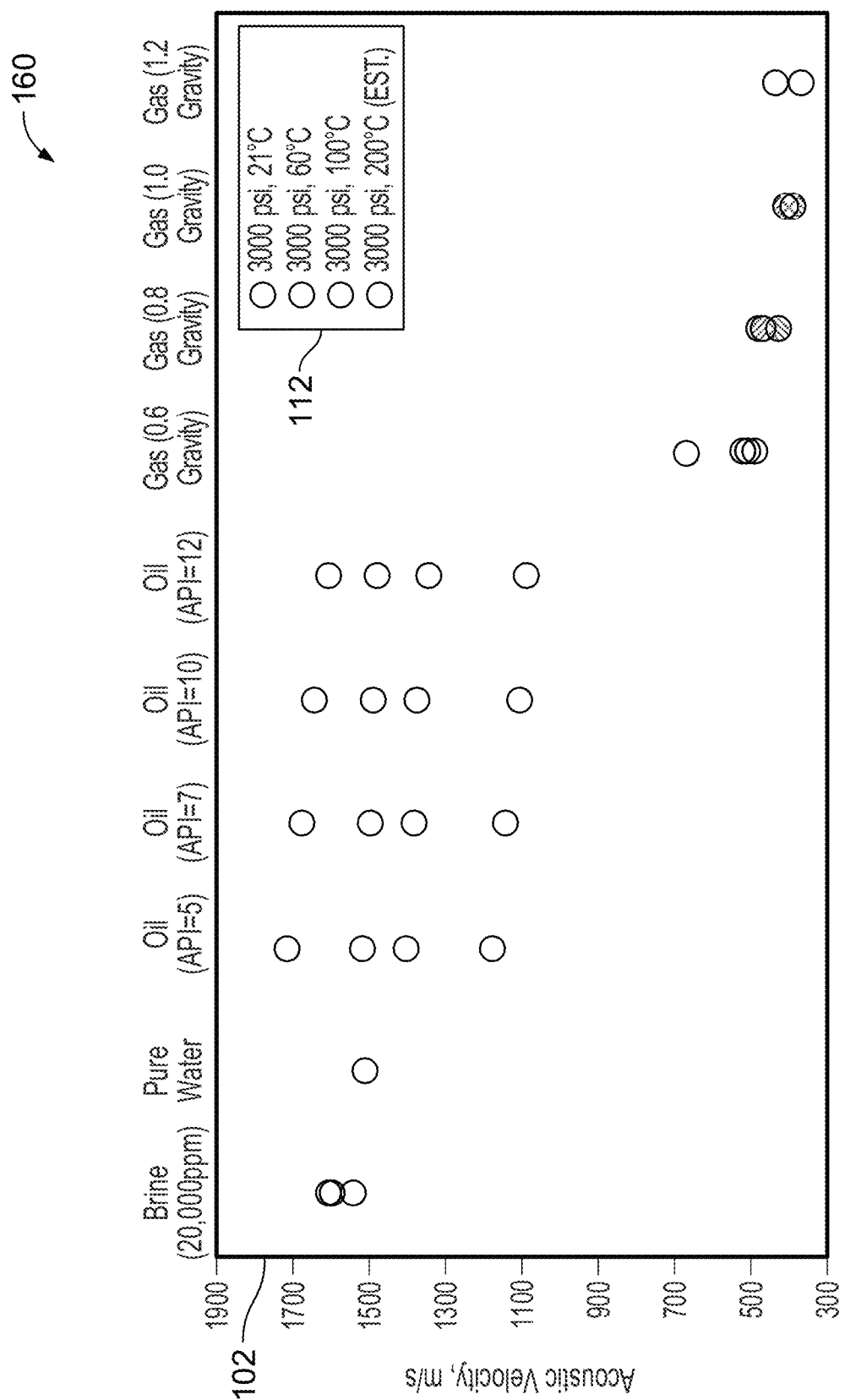
FIG. 4 is a graph 160 that illustrates an example set of empirical relationships among acoustic wave velocity, fluid type, fluid pressure, and fluid temperature for a multiphase fluid.

FIG. 1 illustrates an example fluid analysis system 100 that is designed to accurately determine fluid fractions (for example, fluid holdups) of a multiphase fluid 105 flowing in a horizontal wellbore 101 formed within a rock formation 103. The multiphase fluid 105 includes two or more substantially distinct phases that are each filled with one fluid 107, 109 (for example, oil, gas, or water). In particular, the fluid analysis system 100 is capable of accurately determining a location of a fluid interface 115 (refer to FIGS. 2 and 3) between adjacent phases of the multiphase fluid 105 in order to accurately determine the fluid fractions within the wellbore 101. In the example illustration of FIG. 1, the multiphase fluid 105 is a two-phase fluid that includes a first fluid 107 and a second fluid 109.

The fluid analysis system 100 includes multiple sets 102 (for example, pairs) of parallel acoustic probes 170 that are oriented parallel to a flow direction 111 (for example, an uphole direction) of the multiphase fluid 105 and therefore parallel to the fluid interface 115 between the first and second fluids 107, 109. The parallel acoustic probes 170 are also oriented parallel to a central axis 120 of the fluid analysis system 100. Each set 102 of parallel acoustic probes 170 includes one transducer 104 and one corresponding receiver 106 that is spaced apart from the transducer 104 in an in-line arrangement that is parallel to the fluid interface 115. The transducer 104 receives a sound wave from an acoustic wave generator 146 and transmits the sound wave along the flow direction 111 to interrogate the surrounding multiphase fluid 105. The receiver 106 receives the sound wave from the transducer 104 for the determination of various properties (for example, fluid type and fluid density) of the fluids 107, 109 based, at least in part, on a velocity at which the sound wave travels between the transducer 104 and the receiver 106. Each set 102 of parallel acoustic probes 170 is capable of transmitting and receiving sound waves of only a single, unique frequency such that sound waves associated with one set 102 of parallel acoustic probes 170 are prevented from interfering with sound waves associated with the other sets 102 of parallel acoustic probes 170.

The transducers 104 and the receivers 106 are respectively supported on flexible frame members 108, 110 (for example, bow springs) of adjacent positioning frames 112, 114 (for example, bow centralizers) that are designed to radially center the fluid analysis system 100 within the wellbore 101. Therefore, positions of the frame members 108, 110 determine positions of the transducers 104 and the receivers 106. The frame members 108, 110 are spaced apart from one another substantially equidistantly about a circumference of the positioning frames 112, 114 at angular positions a-d. Within a set 102 of parallel acoustic probes 170, the transducer 104 and the receiver 106 are positioned on corresponding frame members 108, 110 that are located at the same angular position such that the in-line arrangement of the transducer 104 and the receiver 106 is oriented parallel to the fluid interface 115.

Referring to FIG. 2, an even number of at least four sets 102 of parallel acoustic probes 170, together with an evenly distributed spaced angular arrangement of the sets 102 of parallel acoustic probes 170, ensures that, irrespective of a rotational position (for example, an angular position) of the fluid analysis system 100 within the wellbore 101, at least one set 102 of parallel acoustic probes 170 will always be located entirely within each fluid 107, 109 of the multiphase fluid 105. The transducers 104 are typically spaced apart from the corresponding receivers 106 by an axial distance of about 0.1 meters (m) to about 1 m.

Referring again to FIG. 1, the fluid analysis system 100 also includes multiple sets 116 (for example, pairs) of perpendicular acoustic probes 180 that are dedicated to assessment of the fluid interface 115 between the first and second fluids 107, 109. The sets 116 of perpendicular acoustic probes 180 are oriented perpendicular to the flow direction 111 of the multiphase fluid 105, perpendicular to the fluid interface 115, and perpendicular to the central axis 120 of the fluid analysis system 100. Each set 116 of perpendicular acoustic probes 180 includes one transducer 118 and one corresponding receiver 122 that is spaced from the transducer 118 in an in-line arrangement that is perpendicular to the fluid interface 115. The transducer 118 receives a sound wave from the acoustic wave generator 146 and transmits the sound wave along a transverse direction 113 to interrogate the surrounding multiphase fluid 105. The receiver 122 receives the sound wave from the transducer 118 for the determination of a location of the fluid interface 115 based, at least in part, on a time period required for the sound wave to travel from the transducer 118 to the receiver 122 and based on the previously determined velocities at which sound waves traveled through the first fluid 107 and the second fluid 109 between the transducers 104 and the corresponding receivers 106. Each set 116 of perpendicular acoustic probes 180 is capable of transmitting and receiving sound waves of only a single, unique frequency such that sound waves associated with one set 116 of perpendicular acoustic probes 180 are prevented from interfering with sound waves associated with the other sets 116 of perpendicular acoustic probes 180 and prevented from interfering with sound waves associated with the sets 102 of parallel acoustic probes 170.

The transducers 118 and the receivers 122 are respectively supported on oppositely located, flexible frame members 124 (for example, bow springs) of a positioning frame 126 (for example, a bow centralizer). Therefore, positions of the frame members 124 determine positions of the transducers 118 and the receivers 122. Within a set 116 of perpendicular acoustic probes 180, the transducer 118 and the receiver 122 are positioned on frame members 124 that are positioned about 180 degrees(°) apart from each other such that the in-line arrangement of the transducer 118 and the receiver 122 is oriented perpendicular to the fluid interface 115. The sets 116 of the perpendicular acoustic probes 180 are typically spaced apart from the receivers 106 by an axial distance of about 0.1 m to about 1 m.

Furthermore, referring to FIG. 3, at least two sets 116 of perpendicular acoustic probes 180 are supported on the positioning frame 126 and in positions that are perpendicular to each other to ensure that, irrespective of a rotational position of the fluid analysis system 100 within the wellbore 101, at least one set 116 of perpendicular acoustic probes 180 spans the fluid interface 115 for determination of the location of the fluid interface 115. As will be discussed in more detail below, the location of the fluid interface 115 can be used by the fluid analysis system 100 to accurately determine the fluid fractions of the first and second fluids 107, 109.

In addition to the sets 102, 116 of acoustic probes 170, 180, the fluid analysis system 100 includes a control unit 128, multiple flow meters 130 (for example, an array of spinners) supported on frame members 150 of a positioning frame 132, an analysis unit 134, a caliper log 136 (for example, which also helps to centralize the fluid analysis system 100), a gyroscope 138, a pressure sensor 140, and a temperature sensor 142. The fluid analysis system 100 also includes a central rail 144 that extends through the positioning frames 112, 114, 126, 132 to provide structural support for the frame members 108, 110, 124, 150 and to facilitate communication between the acoustic probes 170, 180 and the wave generator 146.

The control unit 128 includes the acoustic wave generator 146 for generating and distributing sound waves of specific frequencies to the transducers 104, 118. The control unit 128 also includes one or more processors 148 at which instructions are executed to control the acoustic wave generator 146. Instructions are also executed at the one or more processors 148 for controlling or otherwise communicating with the various other components of the fluid analysis system 100 through the acoustic wave generator 146.

The flow meters 130 are respectively positioned on the frame members 150 of the positioning frame 132, and angular positions a-d of the frame members 150 correspond to angular positions a-d of the frame members 108, 110 such that each flow meter 130 is associated with a particular set 102 of parallel acoustic probes 170 within one of the fluids 107, 109. In some embodiments, a probing module 190 of the fluid analysis system 100 includes all of the positioning frames 112, 114, 126, 132 and all of the components (for example, the acoustic probes 170, 180 and the flow meters 130) supported thereon. In some embodiments, the probing module 190 typically has a total length of about 0.5 m to about 2 m.

Independent of the activity of the parallel acoustic probes 170, the flow meters 130 can measure the flow rate of the surrounding fluids 107, 109 that flow past the flow meters 130 associated with respective parallel acoustic probes 180. The caliper log 136 can determine a local diameter of the wellbore 101 surrounding the fluid analysis system 100, while the gyroscope 138 can determine a rotational position of the fluid analysis system 100 within the wellbore 101. The analysis unit 134 includes one or more processors 152 by which data received from the receivers 106, the receivers 122, the flow meters 130, the caliper log 136, the gyroscope 138, the pressure sensor 140, and the temperature sensor 142 can be analyzed to identify the first and second fluids 107, 109, to accurately determine the location of the fluid interface 115, and to accurately determine the fluid fractions of the multiphase fluid 105 based on accurately determined location of the fluid interface 115.

In general, an outer diameter of the fluid analysis system 100 should be relatively small when the fluid analysis system 100 is not operational to allow for passage through completion restrictions of varying size. For example, caliper arms may be retracted, and flexible frame members may be extended from inner sides. In some examples, a caliper tool needs to be mechanically robust (for example, strong) in order to withstand contact with a borehole wall (for example, formed of rock, in an openhole), while a holdup tool may not need to be as strong. For instance, contact with a borehole wall can potentially damage a tool or sensor, and thus there is a maximum opening restriction.

In a first step of analyzing the multiphase fluid 105, the first and second fluids 107, 109 can be identified at the analysis unit 134 based on empirical data that provides relationships between a fluid pressure (for example, measured at the pressure sensor 140), a fluid temperature (for example, measured at the temperature sensor 142), and an average velocity within each fluid phase (for example, determined at the analysis unit 134) at which sound waves travel between the transducers 104 and the corresponding receivers 106 within a given fluid 107, 109. FIG. 4 provides a graph 160 that illustrates one example set of empirical relationships among acoustic wave velocity, fluid type, fluid pressure, and fluid temperature. According to such empirical relationships, the fluid type may be determined based on measured values of the acoustic wave velocity, the fluid pressure, and the fluid temperature.

Figure 5:
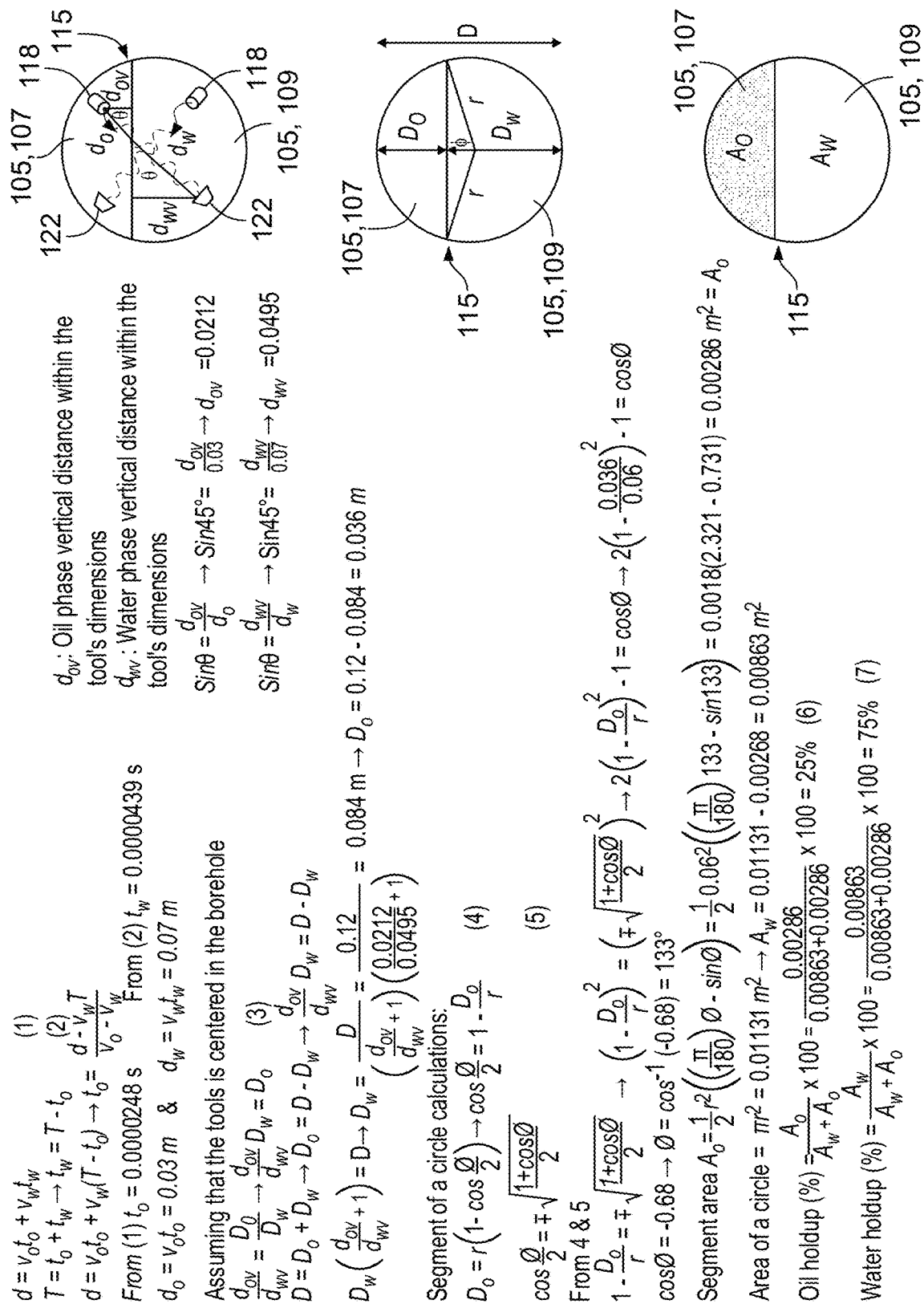
FIG. 5 illustrates an example case for which the fluid analysis system of FIG. 1 is used to characterize a two-phase fluid for which the fluid fractions are one fourth and three fourths within a wellbore.

FIG. 5 illustrates an example case for which the fluids 107, 109 have been respectively identified as oil and water and for which an analysis can be carried out to determine fluid fractions of the oil and water. Assumptions include that neither the oil nor water are present as emulsions, that the fluid analysis system 100 is radially centered within the wellbore 101, that oil accounts for one fourth of a cross-sectional area of the wellbore 101, and that both sets 116 of perpendicular acoustic probes 180 are tilted by an angle θ of about 45° with respect to the gyroscope 138 such that at least one set 116 of perpendicular acoustic probes 180 spans the fluid interface 115 at all times.

The example case includes the following parameters:
D: diameter of wellbore 101 (determined by the caliper 136)
$D_o$: vertical distance of oil (from a top internal surface of the wellbore 101 to the fluid interface 115) within wellbore 101
$D_w$: vertical distance of water (from a bottom internal surface of the wellbore 101 to the fluid interface 115) within wellbore 101
$A_o$: cross-sectional area of oil within wellbore 101
$A_w$: cross-sectional area of water within wellbore 101
d: total distance between a transducer 116 and a corresponding receiver 122
T: total time period required for a sound wave to traverse the distance d $d_o$: distance within oil between the transducer 116 or the corresponding receiver 122 and the fluid interface 115 (along a line extending between the transducer 116 and the corresponding receiver 112)
$d_w$: distance within water between the receiver 122 or the corresponding transducer 116 and the fluid interface 115 (along a line extending between the transducer 116 and the corresponding receiver 112)
$t_o$: time period required for a sound wave to traverse the distance $d_o$;
$t_w$: time period required for a sound wave to traverse the distance $d_w$;
$v_o$: velocity of the sound wave in oil;
$v_w$: velocity of the sound wave in water;

The given parameters for this example case are as follows:
D=0.1 m (determined by the dimensions of the fluid analysis system 100);
T=0.000687 s (determined at the analysis unit 134 from sound waves received at the receiver 122)
$v_o$=1,200 m/s (determined at the analysis unit 134 from sound waves received at receivers 106 (a, b, g, h))
$v_w$=1,600 m/s (determined at the analysis unit 134 from sound waves received at receivers 106 (c, d, e, f)).

The location of the fluid interface 115 can be identified from $D_w$ and $D_o$. From Equations (1)-(3), $D_w$=0.084 m and $D_o$=0.036 m. From Equations (4) and (5), $A_w$=0.00863 m² and $A_o$=0.00286 m². From Equations (5) and (6), the fluid fraction of oil (for example, the oil holdup) can be determined as 25%, and the fluid fraction of water (for example, the water holdup) can be determined as 75%.

In the example embodiment of FIGS. 1-5, the fluid analysis system 100 includes four sets 102 of parallel acoustic probes 170. That is, each probe from sets 116 of perpendicular acoustic probes 180 needs a corresponding set 102 of parallel acoustic probes 170 at the same horizontal position. Therefore, in an example case of two fluids, two sets 116 of perpendicular acoustic probes 180 are needed, resulting in a minimum of four sets 102 of parallel acoustic probes 170. For example, if a set 102 of parallel acoustic probes 170 encounters a sound velocity from oil, then both the transducer 104 and the receiver 106 of the set 102 must be located within the oil, and the corresponding probe 180 (for example, the transducer 118 or the receiver 122) of the set 116 of perpendicular acoustic probes 180 must also be located within the oil. Such a configuration is important for interface estimation. By extension, for three-phase fluid flow, a fluid analysis system as discussed herein would include four sets 116 of perpendicular acoustic probes 180 and at least eight sets 102 of parallel acoustic probes 170.

In the example illustration of FIG. 6, a multiphase fluid 205 is a three-phase fluid that includes a first fluid 207, a second fluid 209, and a third fluid 217 within a wellbore 201 of a rock formation 203. In a three-phase fluid, a fluid analysis system 200 requires additional perpendicular acoustic probes 180 for accurately determining a location of each fluid interface 219, 221 because the two fluid interfaces cannot be determined from a set of perpendicular acoustic probes 180 that cross all three fluids of a multiphase fluid at one time. Therefore, the fluid analysis system 200 includes two first sets 254 (for example, pairs) of perpendicular acoustic probes 180 and two second sets 256 (for example, pairs) of perpendicular acoustic probes 180 for a total of four sets of perpendicular acoustic probes 180.

Referring to FIG. 7, each of the first sets 254 of perpendicular acoustic probes 180 are parallel to each other, and each of the second sets 256 of perpendicular acoustic probes 180 are parallel to each other. Furthermore, the first sets 254 of perpendicular acoustic probes 180 are angularly offset from the second sets 256 of perpendicular acoustic probes 180 by an angle of about 45°. The angular offset ensures that, irrespective of a rotational position of the fluid analysis system 200 within the wellbore 201, at least both of the first sets 254 of the perpendicular acoustic probes 180 or at least both of the second sets 256 of perpendicular acoustic probes 180 will each span only two of the three fluids 207, 209, 217 at any given time.

As discussed above with respect to the perpendicular acoustic probes 180 of the fluid analysis system 100, the perpendicular acoustic probes 180 of the fluid analysis system 200 are oriented perpendicular to a bulk flow direction 211 of the multiphase fluid 205, perpendicular to the fluid interfaces 219 between the first and second fluids 217, 207 and the fluid interface 221 between the second and third fluids 207, 209, and perpendicular to a central axis 220 of the fluid analysis system 200. Each set 254, 256 of perpendicular acoustic probes 180 includes one transducer 118 and one corresponding receiver 122 that is spaced from the transducer 118 in an in-line arrangement that is perpendicular to the fluid interfaces 219, 221. Each set 254, 256 of perpendicular acoustic probes 180 is capable of transmitting and receiving sound waves of only a single, unique frequency such that sound waves associated with one set 254, 256 of perpendicular acoustic probes 180 are prevented from interfering with sound waves associated with the other sets 254, 256 of perpendicular acoustic probes 180 and prevented from interfering with sound waves associated with the sets 102 of parallel acoustic probes 170.

The transducers 118 and the receivers 122 are respectively supported on oppositely located, flexible frame members 224, 264 (for example, bow springs) of positioning frames 226, 266 (for example, bow centralizers). Therefore, positions of the frame members 224, 264 determine positions of the transducers 118 and the receivers 122. As shown in FIG. 7, within a set 254, 256 of perpendicular acoustic probes 180, the transducer 118 and the receiver 122 are positioned on frame members 224, 264 that are positioned about 90° apart from each other such that the in-line arrangement of the transducer 118 and the receiver 122 is oriented perpendicular to the fluid interfaces 219, 221. The sets 254 of perpendicular acoustic probes 180 are typically spaced from the receivers 106 of the sets 116 of parallel acoustic probes 170 by an axial distance of about 0.1 m to about 1 m, and the sets 256 of perpendicular acoustic probes 180 are typically spaced from the sets 254 of perpendicular acoustic probes 180 by an axial distance of about 0.1 m to about 1 m.

Referring to FIGS. 6-9, the fluid analysis system 200 is otherwise substantially similar in construction and function to the fluid analysis system 100. Therefore, the fluid analysis system 200 further includes the control unit 128, the flow meters 130 supported on a positioning frame 232, sets 102 of parallel acoustic probes 170 supported on positioning frames 212, 214 at positions a-h (refer to FIG. 8), the analysis unit 134, the caliper 136, the gyroscope 138, the pressure sensor 140, the temperature sensor 142, and a central support rail (hidden by depiction of the positioning frame members). The receivers 122 of the sets 254, 256 of perpendicular acoustic probes 180 receive sound waves from the corresponding transducers 118 for the determination of locations of the fluid interfaces 219, 221 based, at least in part, on time periods required for sound waves to travel from the transducers 118 to the receivers 122 and based on the previously determined velocities at which sound waves traveled through the fluids 207, 209, 217. In some embodiments, a probing module 290 of the fluid analysis system 200 includes all of the positioning frames 112, 114, 126, 226, 266 and all of the components (for example, the acoustic probes 170, 180 and the flow meters 130) supported thereon. In some embodiments, the probing module 290 typically has a total length of about 0.5 m to about 2.5 m.

FIGS. 6-9 illustrate an example case for which the fluids 207, 209, 217 have been identified respectively as gas, oil, and water using wave velocities determined with the sets 102 of parallel acoustic probes 170 and empirical data, such as the example relationships provided in the graph 160. The analysis discussed above with respect to FIG. 5 can be adapted to the three-phase fluid 205 and the fluid analysis system 200 to determine fluid fractions of the oil, water, and gas within the wellbore 201. Assumptions include that none of the fluids 207, 209, 217 are present as emulsions and that the fluid analysis system 200 is radially centered within the wellbore 201.

In addition to parameters that are analogous to those discussed above with respect to the analysis of FIG. 5, an example case related to the illustration of FIG. 6 includes the following parameters:
$A_o$: cross-sectional area of oil within wellbore 201
$A_w$: cross-sectional area of water within wellbore 201
$A_g$: cross-sectional area of gas within wellbore 201.
In the analysis of the three-phase fluid 205, $A_w$ and $A_g$ must be calculated first, and then $A_o$ (for example, the middle fluid phase) can be determined from $A_w$, $A_g$, and a known total cross-sectional area of the wellbore 201.

In some embodiments, a fluid analysis system with a relatively compact design may provide more accurate measurements due to the acoustic probes being located relatively close to each other. For example, FIG. 10 illustrates a fluid analysis system 300 that has such a design. The fluid analysis system 300 is substantially similar in construction and function to the fluid analysis system 100, except that sets 302 (for example, pairs) of parallel acoustic probes 170, sets 316 (for example, pairs) of perpendicular acoustic probes 180, and the flow meters 130 are all supported on the same, single set of inflexible (for example, rigid) frame members 392 of a positioning frame 374. The positioning frame 374 also includes flexible frame members 372 (for example, bow springs) that are located at opposite ends of the inflexible frame members 392 and that terminate along a central support rail 344. The inflexible frame members 392 are supported on the flexible frame members 372. The rigidity of the frame members 392 ensures that the acoustic probes 170, 180 and the flow meters 130 can move only within degrees of freedom allowed by the flexible frame members 372 and therefore that any associated measurements are accurately attributed to a selected, intended phase within a multiphase fluid.

In some embodiments, a probing module 390 of the fluid analysis system 300 includes the positioning frame 374 and all of the components (for example, the acoustic probes 170, 180 and the flow meters 130) supported thereon. In some embodiments, the probing module 390 typically has a total length of about 0.5 m to about 1 m. In general, the shorter a length of a fluid analysis system, the better. For example, shorter tools can be run more easily, and the shorter a tool, the more consistent are the measurements between different modules and sensors, such that data from different modules and sensors can be integrated.

In some embodiments, since the vertical distance between the transducer and the receiver in the set 316 of perpendicular acoustic probes 180 is prone to dynamic changes as the fluid analysis system 300 moves through the borehole (for example, which causes the flexible frame members 372 to compress and expand to accommodate borehole irregularities), it is necessary to have a very sensitive electronic sensor that can measure +/−changes in vertical distance and incorporate these changes into the calculations for the parameter d. For example, in some embodiments, the fluid analysis system 300 further includes a vertical distance change sensor set 398 that is composed of a tensioned string 394 that is fixed at one end and that is attached to a reel drum 396 with a spiral spring at the other end for maintaining the string 394 in tension. An electronic sensor attached to the drum 396 can measure +/−drum movements. In some embodiments, each set of perpendicular acoustic probes may be provided with a laterally adjacent corresponding vertical distance change sensor set 398 for such a purpose.

Fluid holdup is a useful parameter that reservoir engineers can use to examine the performance of a reservoir, to diagnose a reservoir operational problem, and to determine a well trajectory. For example, very high water holdup can reduce well productivity and even choke a well. Fluid holdup can also be used to cross check the performance of spinner arrays (for example, gas should flow faster than water). In general, fluid holdup, along with spinner readings and a borehole size (for example, determined from a caliper log), can be used to calculate a flow rate of each fluid phase along a borehole.

The inclusion of the sets 116, 254, 256, 316 of perpendicular acoustic probes 180 within the fluid analysis systems 100, 200, 300 allows for accurate determination of fluid interface locations in order to accurately determine fluid fractions within a wellbore. In contrast, conventional systems may include only parallel acoustic probes and do not additionally include perpendicular acoustic probes. Such conventional systems, having no components dedicated specifically to the assessment of fluid interfaces, cannot accurately determine fluid interface locations. Rather, such systems can only roughly estimate fluid interface locations using parallel acoustic probes. Inaccurate estimates of fluid interface locations can lead to inaccurate calculations of fluid fractions within a wellbore, inaccurate estimation of fluid flows within a wellbore, and eventually inaccurate individual fluid flows at the surface.

Figure 11:
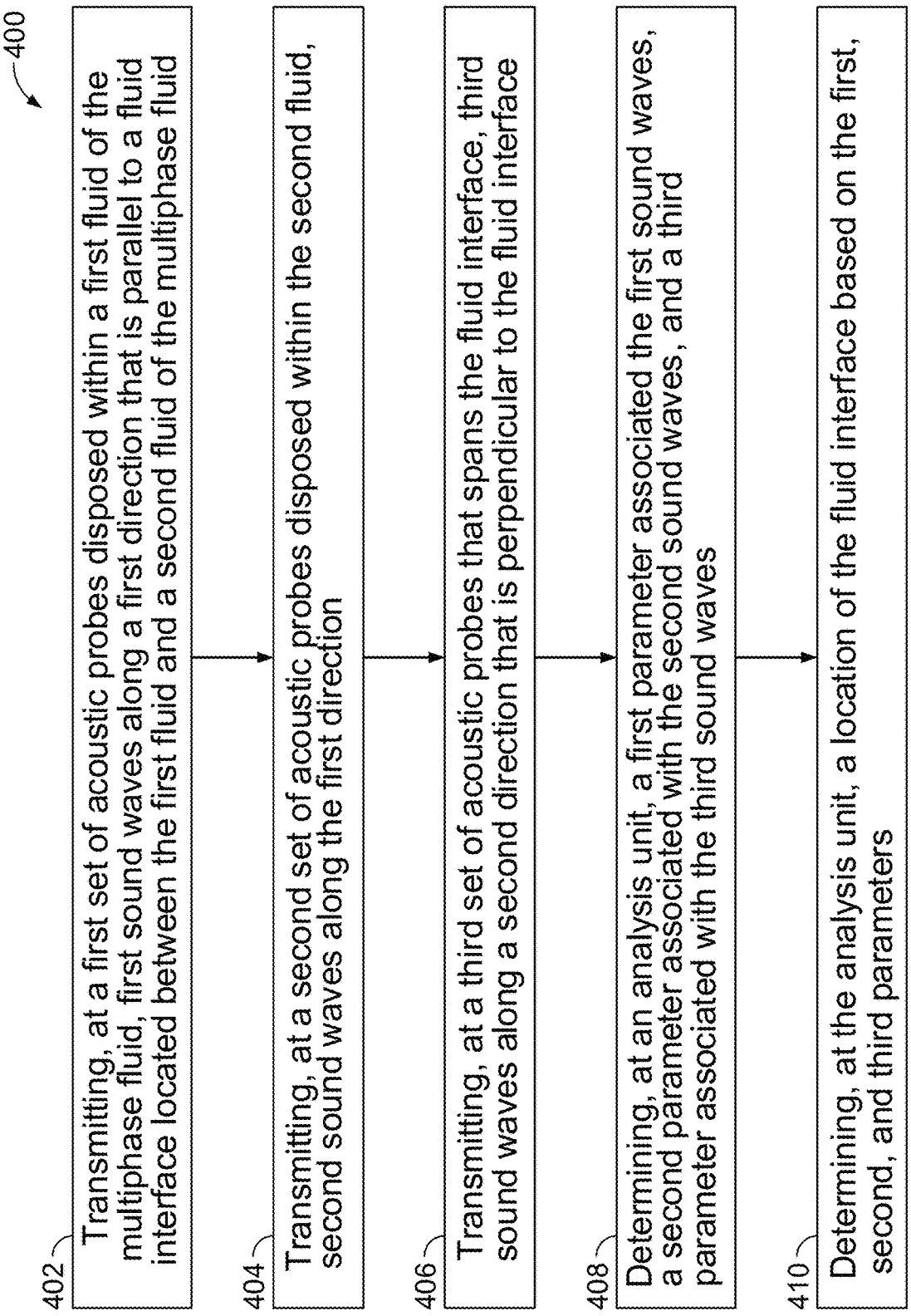
FIG. 11 is a flow chart illustrating an example method of characterizing a multiphase fluid within a borehole using a fluid analysis system.

FIG. 11 is a flow chart illustrating an example method 400 of characterizing a multiphase fluid (for example, the multiphase fluid 105, 205) within a borehole (for example, the wellbore 101, 201). In some embodiments, the method 400 includes a step 402 for transmitting, at a first set of acoustic probes (for example, the set 102, 302 of parallel acoustic probes 170) disposed within a first fluid (for example, the first fluid 107, 207) of the multiphase fluid, first sound waves along a first direction (for example, the flow direction 111, 211) that is parallel to a fluid interface (for example, the fluid interface 115, 219) located between the first fluid and a second fluid (for example, the second fluid 109, 209) of the multiphase fluid. In some embodiments, the method 400 includes a step 404 for transmitting, at a second set of acoustic probes (for example, the set 102, 302 of parallel acoustic probes 170) disposed within the second fluid, second sound waves along the first direction. In some embodiments, the method 400 includes a step 406 for transmitting, at a third set of acoustic probes (for example, the set 116, 254, 256, 316 of perpendicular acoustic probes 180) that spans the fluid interface, third sound waves along a second direction (for example, the transverse direction 113) that is perpendicular to the fluid interface. In some embodiments, the method 400 includes a step 408 for determining, at an analysis unit (for example, the analysis unit 134), a first parameter associated the first sound waves, a second parameter associated with the second sound waves, and a third parameter associated with the third sound waves. In some embodiments, the method 400 includes a step 410 for determining, at the analysis unit, a location of the fluid interface based on the first, second, and third parameters.

While the fluid analysis systems 100, 200, 300 have been described and illustrated with respect to certain dimensions, sizes, shapes, arrangements, materials, and methods 400, in some embodiments, a fluid analysis system that is otherwise substantially similar in construction and function to any of the fluid analysis systems 100, 200, 300 may include one or more different dimensions, sizes, shapes, arrangements, configurations, and materials or may be utilized according to different methods. Accordingly, other embodiments are also within the scope of the following claims.

What is claimed is:

1. A fluid analysis system for characterizing a multiphase fluid, the fluid analysis system comprising:
a first set of acoustic probes disposed at a first angular position about a central axis of the fluid analysis system and oriented to direct first sound waves along a first direction that is parallel to the central axis;
a second set of acoustic probes disposed at a second angular position about the central axis that is opposite to the first angular position and oriented to direct second sound waves along the first direction;
a third set of acoustic probes spanning the central axis and oriented to direct third sound waves along a second direction that is perpendicular to the central axis; and
an analysis unit configured to:
determine a first parameter associated with the first sound waves, a second parameter associated with the second sound waves, and a third parameter associated with the third sound waves, and
determine a location of a fluid interface within the multiphase fluid based on the first, second, and third parameters.

2. The fluid analysis system of claim 1, wherein the analysis unit is further configured to determine a first fluid fraction of a first fluid of the multiphase fluid and a second fluid fraction of a second fluid of the multiphase fluid based on the location of the fluid interface.

3. The fluid analysis system of claim 1, wherein the first and second sets of acoustic probes are located at a first axial position along the central axis.

4. The fluid analysis system of claim 3, wherein the third set of acoustic probes is located at a second axial position along the central axis that is spaced apart from the first axial position.

5. The fluid analysis system of claim 1, wherein the first set of acoustic probes comprises a first transducer and a first receiver that are tuned to a first unique frequency, wherein the second set of acoustic probes comprises a second transducer and a second receiver that are tuned to a second unique frequency, and wherein the third set of acoustic probes comprises a third transducer and a third receiver that are tuned to a third unique frequency.

6. The fluid analysis system of claim 5, wherein the first parameter comprises a first velocity at which the first sound waves travel between the first transducer and the first receiver, and wherein the second parameter comprises a second velocity at which the second sound waves travel between the second transducer and the second receiver.

7. The fluid analysis system of claim 6, wherein the third parameter comprises a time period taken for the third sound waves to travel between the third transducer and the third receiver.

8. The fluid analysis system of claim 7, wherein the analysis unit is further configured to determine a first distance traveled by the third waves between the third transducer and the fluid interface and a second distance traveled by the third waves between the fluid interface and the third receiver to define the location of the fluid interface.

9. The fluid analysis system of claim 8, wherein the analysis unit is further configured to determine a first fluid fraction of a first fluid of the multiphase fluid and a second fluid fraction of a second fluid of the multiphase fluid based on the first and second distances traveled by the third waves.

10. The fluid analysis system of claim 1, further comprising a fourth set of acoustic probes spanning the central axis.

11. The fluid analysis system of claim 10, wherein the third and fourth sets of acoustic probes are located at the same axial position along the central axis, and wherein the fourth set of acoustic probes is oriented to direct fourth sound waves along a third direction that is perpendicular to the central axis of the fluid analysis system and perpendicular to the second direction.

12. The fluid analysis system of claim 10, wherein the third and fourth sets of acoustic probes are both located at a first axial position along the central axis, and wherein the fourth set of acoustic probes is oriented to direct fourth sound waves along the second direction.

13. The fluid analysis system of claim 12, further comprising a fifth set of acoustic probes and a sixth set of acoustic probes that are both located at a second axial position along the central axis that is different from the first axial position and that are oriented to respectively direct fifth and sixth sound waves along a third direction that is perpendicular to the central axis of the fluid analysis system and that is angularly offset from the second direction.

14. The fluid analysis system of claim 13, wherein the fluid interface is a first fluid interface at a first location, and wherein the analysis unit is further configured to determine a second location of a second fluid interface within the multiphase fluid.

15. The fluid analysis system of claim 1, further comprising a wave generator that transmits the first, second, and third sound waves respectively to the first, second, and third sets of acoustic probes.

16. The fluid analysis system of claim 1, further comprising a gyroscope that determines a rotational position of the fluid analysis system within a borehole.

17. A method of characterizing a multiphase fluid within a borehole, the method comprising:

transmitting, at a first set of acoustic probes disposed within a first fluid of the multiphase fluid, first sound waves along a first direction that is parallel to a fluid interface located between the first fluid and a second fluid of the multiphase fluid;

transmitting, at a second set of acoustic probes disposed within the second fluid, second sound waves along the first direction;

transmitting, at a third set of acoustic probes that spans the fluid interface, third sound waves along a second direction that is perpendicular to the fluid interface;

determining, at an analysis unit, a first parameter associated the first sound waves, a second parameter associated with the second sound waves, and a third parameter associated with the third sound waves; and determining, at the analysis unit, a location of the fluid interface based on the first, second, and third parameters.

18. The method of claim 17, further comprising determining, at the analysis unit, a first fluid fraction of the first fluid and a second fluid fraction of the second fluid based on the location of the fluid interface.

19. The method of claim 17, wherein the first parameter comprises a first velocity at which the first sound waves travel within the first fluid, and wherein the second parameter comprises a second velocity at which the second sound waves travel within the second fluid.

20. The method of claim 19, wherein the third set of acoustic probes comprises a transducer and a receiver, and wherein the third parameter comprises a time period taken for the third sound waves to travel between the transducer and the receiver.

21. The method of claim 20, further comprising determining, at the analysis unit, a first distance traveled by the third waves between the transducer and the fluid interface and a second distance traveled by the third waves between the fluid interface and the receiver to define the location of the fluid interface.

22. The method of claim 21, further comprising determining, at the analysis unit, a first fluid fraction of the first fluid and a second fluid fraction of the second fluid based on the first and second distances traveled by the third waves.

23. The method of claim 17, further comprising transmitting the first, second, and third sound waves from a wave generator respectively to the first, second, and third sets of acoustic probes.

24. The method of claim 17, further comprising determining, at a gyroscope, a rotational position of the fluid analysis system within the borehole.

* * * * *